(12) United States Patent
Eickmann et al.

(10) Patent No.: US 6,258,363 B1
(45) Date of Patent: Jul. 10, 2001

(54) *VARICELLA ZOSTER* VIRUS (VZV) IMMUNOREACTIVE PROTEIN VP26 AND ITS DIAGNOSTIC USE

(75) Inventors: Markus Eickmann, Marburg; Dorothee Gicklhorn, Gladenback; Klaus Radsak, Marburg; Hans-Peter Hauser, Elnhausen; Bernhard Giesendorf, Michelbach, all of (DE)

(73) Assignee: Dade Behring Marburg GmbH, Marburg (DE)

( * ) Notice: Subject to any disclaimer, the term of this patent is extended or adjusted under 35 U.S.C. 154(b) by 0 days.

(21) Appl. No.: 09/219,337

(22) Filed: Dec. 23, 1998

(30) Foreign Application Priority Data

Dec. 23, 1997 (DE) ............................... 197 57 765

(51) Int. Cl.⁷ ........................... A61K 39/245; C12Q 1/70
(52) U.S. Cl. .................................. 424/230.1; 424/204.1; 435/5; 435/7.92; 435/7.93; 530/300; 536/23.72
(58) Field of Search ............................ 435/5, 7.92, 7.93; 530/300; 536/23.72; 424/230.1, 204.1

(56) References Cited

PUBLICATIONS

M.D. Davison et al., "Identification of genes encoding two capsid proteins (VP24 and VP26) of herpes simplex virus type 1", J. Gen Virology, (1992), 73 pp. 2709–2713.

A.J. Davison et al., "J. Gen. Virol., vol. 67", *The Complete DNA Sequence of Varicella–Zoster Virus*, pp. 1759–1816, (1986).

D.R. Harper et al., "The Journal of Infectious Diseases", vol. 159 No. 3, IgM and IgG Responses to Varicella–Zoster Virus p32/p36 Complex After Chickenpox and Zoster, Congenital and Subclinical Infections, and Vaccination, pp. 444–451, (Mar. 1989).

A. Vafai et al., "Virus Research", vol. 15, Antigenic cross–reaction between a varicella–zoster virus nucleocapsid protein encoded by gene 40 and a herpes simplex virus nucleocapsid protein, pp. 163–174 (1990).

*Primary Examiner*—Ali R. Salimi
(74) *Attorney, Agent, or Firm*—Heller Ehrman White & McAuliffe LLP

(57) ABSTRACT

*Varicella zoster* virus (VZV) immunoreactive protein VP26 and its diagnostic use are described. The invention relates to immunoreactive peptides which are homologous with the region of amino acid positions 12 to 235 of the *varicella zoster* virus protein VP26, to nucleic acids which encode these peptides and to the use of the peptides or nucleic acids for diagnosing an infection with *varicella zoster* virus.

5 Claims, 5 Drawing Sheets

FIG. 1(a)

```
     ATGACACAACCCGCATCGTCTCGTGTAGTCTTTGATCCCAGCAACCCCACCACATTTTCG
1    ------+---------+---------+---------+---------+---------+    60
     TACTGTGTTGGGCGTAGCAGAGCACATCAGAAACTAGGGTCGTTGGGGTGGTGTAAAAGC
     MetThrGlnProAlaSerSerArgValValPheAspProSerAsnProThrThrPheSer
     M   T   Q   P   A   S   S   R   V   V   F   D   P   S   N   P   T   T   P   S

GTGGAAGCAATTGCGGCTTACACCCCCGTTGCTTTAAATACGACTTTTAAACGCCAGTGGA
61   ------+---------+---------+---------+---------+---------+   120
     CACCTTCGTTAACGCCGAATGTGGGGCAACGAAATTATGCTGAAAATTTGCGGTCACCT
     ValGluAlaIleAlaAlaTyrThrProValAlaLeuIleArgLeuLeuAsnAlaSerGly
     V   E   A   I   A   A   Y   T   P   V   A   L   I   R   L   L   N   A   S   G

CCTTTGCAACCTGGTCACCGTGGACATCGCTGATGCCAGAAGCATTTACACCGTGGGA
121  ------+---------+---------+---------+---------+---------+   180
     GGAAACGTTGGACCAGTGGCACACCTGTAGCGACTACGGTCTTCGTAAATGTGGCACCCT
     ProLeuGlnProGlyHisArgValAspIleAlaAspAlaAlaArgSerIleTyrThrValGly
     P   L   Q   P   G   H   R   V   D   I   A   D   A   R   S   I   Y   T   V   G

GCCGCGGGCCAGTGCCGCGCGCACGTGCCGCACGCGCTAACCATAATGCAAATACGCCGAACG
181  ------+---------+---------+---------+---------+---------+   240
     CGGCGCCCGGTCACGGCGCGCGTGCACGGCGCGATTGGTATTACGTTTATGCTTATGCGGCTTGC
     AlaAlaAlaSerAlaAlaArgAlaAlaArgAlaAsnHisAsnAlaAsnThrIleArgArgThr
     A   A   A   S   A   A   R   A   R   A   N   H   N   A   N   T   I   R   R   T

GCCATGTTTGCCGAGACTGACCCTATGACATGGTTAAGACCAACGGTTGGCTTAAAACGT
241  ------+---------+---------+---------+---------+---------+   300
     CGGTACAAACGGCTCTGACTGGATACTGTACCAATTCTGGTTGCCAACCGAATTTGCA
     AlaMetPheAlaGluThrAspProMetThrTrpLeuArgProThrValGlyLeuLysArg
     A   M   F   A   E   T   D   P   M   T   W   L   R   P   T   V   G   L   K   R
```

FIG. 1(b)

```
301  ACGTTTAACCCGCGTATTATACGACCACAACCCCCAAATCCATCCATGAGTTTGGGAATC
     ---------+---------+---------+---------+---------+---------+   360
     TGCAAATTGGGCGCATAATATGCTGGTGTTGGGGGTTTAGGTAGGTACTCAAACCCTTAG
     ThrPheAsnProArgIleIleArgProGlnProProAsnProSerMetSerLeuGlyIle
      T  F  N  P  R  I  I  R  P  Q  P  P  N  P  S  M  S  L  G  I

361  TCGGGGCCTACTATATTGCCGCAAAAACACAGAGCGCCGATCAGTCTGCTTTACAACAG
     ---------+---------+---------+---------+---------+---------+   420
     AGCCCCGGATGATATAACGGCGTTTTTGTGTCTCGCGGCTAGTCAGACGAAATGTTGTC
     SerGlyProThrIleLeuProGlnLysThrGlnSerAlaAspGlnSerAlaLeuGlnGln
      S  G  P  T  I  L  P  Q  K  T  Q  S  A  D  Q  S  A  L  Q  Q

421  CCCGCCGCGTTGGCGTTTCGGATCATCCCCGCAACACCCCACCTCAAACGACGTCG
     ---------+---------+---------+---------+---------+---------+   480
     GGGCGGCGCAACCGCAAAAGCCCTAGTAGGGCCGTTGTGGGGGTGGAGTTTGCTGCAGC
     ProAlaAlaLeuAlaPheSerGlySerSerProGlnHisProProGlnThrThrSer
      P  A  A  L  A  F  S  G  S  S  P  Q  H  P  P  Q  T  T  S

481  GCATCCGTTGGACAACAGCAACACGTGGTCGGGGTCTTCTGGACAACAACCGCAACAG
     ---------+---------+---------+---------+---------+---------+   540
     CGTAGGCAACCTGTTGTCGTTGTGCACCAGCCCCAGAAGACCTGTTGTTGGCGTTGTC
     AlaSerValGlyGlnGlnHisValSerGlySerGlyGlnProGlnGlnProGlnGln
      A  S  V  G  Q  Q  H  V  V  S  G  S  S  G  Q  Q  P  Q  Q

541  GGAGCACAGTCAAGCACTGTCCAGCCAACAACCGGATCACCGCCCGCGGCCCAAGGCGTG
     ---------+---------+---------+---------+---------+---------+   600
     CCTCGTGTCAGTTCGTGACAGGTCGGTTGTTGGCCTAGTGGCGGGCGCCGGGTTCCGCAC
     GlyAlaGlnSerSerThrValGlnProThrThrGlySerProProAlaAlaGlnGlyVal
      G  A  Q  S  S  T  V  Q  P  T  T  G  S  P  P  A  A  Q  G  V
```

FIG. 1(c)

```
       CCACAGTCTACCCCGCCCCCAACCCCAAATACCCCCCAGGGGGGTAAGGGACAGACCTTG
601    ---------+---------+---------+---------+---------+---------+  660
       GGTGTCAGATGGGGCGGGGGTTGGGTTTATGGGGGTCCCCATTCCCTGTCTGGAAC
       ProGlnSerThrProProProThrGlnAsnThrProGlnGlyGlyLysGlyGlnThrLeu
        P  Q  S  T  P  P  P  T  Q  N  T  P  Q  G  G  K  G  Q  T  L

TCACACACGGGACAATCTGGAAACGCTTCAAGAAGTCGTAGGGTG
661    ---------+---------+---------+---------+-----  705
       AGTGTGTGCCCTGTTAGACCTTTGCGAAGTTCTTCAGCATCCCAC
       SerHisThrGlyGlnSerGlyAsnAlaSerArgSerArgArgVal
        S  H  T  G  Q  S  G  N  A  S  R  S  R  R  V
```

FIG. 2

| NO. | STATUS | ELISA IgM REF-ERENCE | ELISA IgM pMal-VP26* 1µm/ml | ELISA IgM pQE-VP26* 1µg/ml | NO. | STATUS | ELISA IgM REF-ERENCE | ELISA IgM pMal-VP26* 1µm/ml | ELISA IgM pQE-VP26* 1µg/ml |
|---|---|---|---|---|---|---|---|---|---|
| | | CONJ. 1:50 | CONJ. 1:50 | CONJ. 1:25 | | | CONJ. 1:50 | CONJ. 1:50 | CONJ. 1:25 |
| | | SERUM 1:42 | SERUM 1:168 | SERUM 1:168 | | | SERUM 1:42 | SERUM 1:168 | SERUM 1:168 |
| 1 | − | 11 | 86 | 62 | 29 | − | 16 | 19 | 104 |
| 2 | − | 22 | 38 | 100 | 30 | − | 8 | 13 | 44 |
| 3 | − | 16 | 31 | 72 | 31 | − | 3 | 23 | 47 |
| 4 | − | 57 | 23 | 88 | 32 | − | 50 | 23 | 101 |
| 5 | + | 133 | 399 | 88 | 33 | − | 9 | 32 | 117 |
| 6 | − | 0 | 161 | 118 | 34 | + | 250 | 187 | 204 |
| 7 | − | 10 | 28 | 77 | 35 | + | 291 | 1079 | 470 |
| 8 | − | 47 | 45 | 60 | 36 | − | 26 | 52 | 44 |
| 9 | − | 7 | 16 | 63 | 37 | + | 139 | 66 | 123 |
| 10 | + | 132 | 173 | 160 | 38 | − | 38 | 87 | 49 |
| 11 | − | 71 | 117 | 70 | 39 | − | 26 | 25 | 40 |
| 12 | − | 0 | 32 | 75 | 40 | − | 49 | 13 | 63 |
| 13 | − | 17 | 75 | 66 | 41 | − | 5 | 20 | 34 |
| 14 | − | 11 | 16 | 57 | 42 | − | 27 | 43 | 80 |
| 15 | − | 23 | 27 | 73 | 43 | − | 51 | 49 | 161 |
| 16 | − | 11 | 27 | 59 | 44 | − | 8 | 38 | 100 |
| 17 | + | 979 | 1720 | 532 | 45 | − | 21 | 38 | 133 |
| 18 | − | 9 | 18 | 44 | 46 | − | 10 | 33 | 82 |
| 19 | − | 34 | 30 | 71 | 47 | − | 29 | 18 | 35 |
| 20 | + | 293 | 630 | 215 | 48 | − | 30 | 66 | 97 |
| 21 | + | 126 | 139 | 259 | 49 | − | 21 | 35 | 97 |
| 22 | − | 61 | 277 | 169 | 50 | − | 56 | 64 | 82 |
| 23 | + | 292 | 808 | 154 | 51 | − | 5 | 40 | 56 |
| 24 | + | 581 | 98 | 115 | 52 | − | 97 | 55 | 37 |
| 25 | + | 321 | 821 | 304 | 53 | − | 2 | 19 | 35 |
| 26 | + | 509 | 519 | 375 | 54 | − | 31 | 21 | 39 |
| 27 | + | 298 | >2500 | 694 | | | | | |
| 28 | − | 29 | 36 | 29 | | | | | |

FIG. 3

| NO. | STATUS | ELISA IgG REFERENCE | ELISA IgG pMal-VP26* 1μm/ml | ELISA IgG pQE-VP26* 2μg/ml | NO. | STATUS | ELISA IgG REFERENCE | ELISA IgG pMal-VP26* 1μm/ml | ELISA IgG pQE-VP26* 2μg/ml |
|---|---|---|---|---|---|---|---|---|---|
|  |  | CONJ. 1:50 | CONJ. 1:50 | CONJ. 1:50 |  |  | CONJ. 1:50 | CONJ. 1:50 | CONJ. 1:50 |
|  |  | SERUM 1:231 | SERUM 1:100 | SERUM 1:100 |  |  | SERUM 1:231 | SERUM 1:100 | SERUM 1:100 |
| 1 | + | 1014 | 176 | 137 | 28 | + | 549 | 89 | 172 |
| 2 | + | 302 | 87 | 356 | 29 | − | 34 | 87 | 120 |
| 3 | + | 642 | 97 | 314 | 30 | − | 76 | 55 | 128 |
| 4 | + | 612 | 87 | 0 | 31 | − | 0 | 38 | 101 |
| 5 | + | 1383 | 181 | 215 | 32 | − | 41 | 94 | 116 |
| 6 | + | 930 | 132 | 118 | 33 | − | 8 | 147 | 177 |
| 7 | + | 653 | 39 | 145 | 34 | + | 1315 | 860 | 340 |
| 8 | + | 915 | 47 | 469 | 35 | + | 1629 | 282 | 187 |
| 9 | + | 570 | 23 | 220 | 36 | + | 469 | 218 | 287 |
| 10 | + | 1770 | 131 | 253 | 37 | + | 693 | 181 | 346 |
| 11 | + | 990 | 104 | 76 | 38 | + | 1449 | 296 | 169 |
| 12 | + | 698 | 227 | 335 | 39 | + | 1139 | 85 | 193 |
| 13 | + | 141 | 62 | 501 | 40 | + | 1509 | 64 | 118 |
| 14 | + | 338 | 39 | 44 | 41 | + | 457 | 110 | 159 |
| 15 | + | 556 | 113 | 246 | 42 | + | 343 | 304 | 545 |
| 16 | + | 791 | 45 | 423 | 43 | + | 1455 | 511 | 244 |
| 17 | + | 2982 | 264 | 258 | 44 | + | 1030 | 174 | 245 |
| 18 | + | 1205 | 192 | 295 | 45 | + | 528 | 50 | 184 |
| 19 | + | 694 | 80 | 100 | 46 | + | 510 | 161 | 353 |
| 20 | + | 1143 | 270 | 340 | 47 | + | 300 | 94 | 290 |
| 21 | + | 1405 | 377 | 256 | 48 | + | 490 | 91 | 157 |
| 22 | + | 539 | 42 | 72 | 49 | + | 888 | 348 | 277 |
| 23 | + | 2449 | 533 | 530 | 50 | + | 1301 | 83 | 195 |
| 24 | + | 1923 | 1117 | 620 | 51 | + | 704 | 247 | 139 |
| 25 | + | 1420 | 95 | 54 | 52 | + | 2523 | 2325 | 757 |
| 26 | PRIMARY + | 1194 | 277 | 66 | 53 | + | 447 | 99 | 153 |
| 27 | ZOSTER + | 2087 | 341 | 204 | 54 | + | 848 | 149 | 167 |

US 6,258,363 B1

VARICELLA ZOSTER VIRUS (VZV) IMMUNOREACTIVE PROTEIN VP26 AND ITS DIAGNOSTIC USE

FIELD OF THE INVENTION

The present invention relates to immunoreactive peptides that are homologous with the region of amino acid positions 12 to 235 of the *varicella zoster* virus protein VP26, to nucleic acids which encode these peptides and to the use of the peptides and nucleic acids for diagnosing an infection with *varicella zoster* virus.

BACKGROUND OF THE INVENTION

In accordance with the classification of the International Committee on Taxonomy of Viruses (ICTV), Van Zoute Vin (VZV) is assigned to the Herpesviridae family. In 75% of cases, primary infections take place not later than the age of 15 and usually take an asymptomatic course. By contrast, infection of adults who have not previously had any contact with the virus and in persons who are naturally or therapeutically immunosuppressed can be associated with severe symptoms. Infection of the fetus also leads to severe symptoms since the virus is able to cross the placenta, and maternal antibodies afford no protection at this time. Following primary infection, the virus persists throughout life in sensory ganglia. After reactivation, the VZV spreads over the peripheral nerves in sensory ganglia and then gives rise to herpes zoster.

Seventy open reading frames (ORF), including the open reading frames for the known glycoproteins gpI (ORF 68), gpII (ORF 31), gpIII (ORF 37), gpIV (ORF 67), gpV (ORF 14) and gpVI (ORF 60), can be deduced from the sequence of the VZV genome, which has been completely elucidated and has a length of 124,884 bp (Dumas strain; (A. J. Davison & J. E. Scott (1986), J. Gen. Virol. 67, 1759–1816)). In each case, the amino acid sequence deduced from the nucleotide sequence displays differing degrees of homology with glycoproteins gE, gB, gH, gI, gC and gL of herpes simplex virus (HSV). However, there is nothing to suggest that the sequence homology can also imply a homologous function. The open reading frames of glycoproteins gpI, gpII, gpIII and gpV have been confirmed by means of molecular biology.

Only a few immunogenic VZV capsid proteins have been identified and characterized. D. R. Harper and C. Grose ((1989), J. Infect. Dis. 159, 444–451) describe immunoreactivity of the p32/p36 complex, which is assigned to the nucleocapsid. In addition, A. Vafai et al. ((1990), Virus Res. 15, 163–174) describe cross reactivity of human VZV-reactive sera, which recognize both the *varicella zoster* virus nucleocapsid protein and the HSV nucleocapsid protein. None of the authors propose an approach that would make it possible to use these antigens in diagnostic test methods.

There are a very large number of different serological methods for checking the level of VZV-specific immunity. Such methods range from radioimmunoassay (RIA), enzyme-linked immunosorbent assay (ELISA), fluorescent-antibody membrane antigen assay (FAMA) and the immunofluorescence test (IFT) to complement fixation (CF). Most of those methods detect VZV-specific antibodies. Virus material which has been isolated following elaborate cultivation on human fibroblast cultures, and which has been prepared for diagnostic use in accordance with special methods, is frequently employed as the antigen.

The isolation of VZV antigens from infected fibroblasts is associated with the risk of infecting personnel who are entrusted with this task. In addition, preparation of antigens is very costly and time-consuming because the virus is not released from infected cells, and special purification methods are therefore required. When the antigen is to be used without prior purification for an immunochemical test, VZV-infected cells are disrupted by sonication, and the antigen is employed directly after dilution for coating microtitration plates, for example. In this method, primarily cell-specific antigens are bound to microtitration plate wells in addition to virus-specific antigens. Accordingly, cell-specific antigens can, particularly in association with certain diseases, for example autoimmune diseases, give rise to false-positive results and consequently to erroneous diagnoses. Other test methods that are based on use of purified viral glycoproteins, such a glycoprotein ELISA, require purification methods which, to a marked degree, are more elaborate and involve heavier losses, so that it has so far scarcely been possible to establish immunochemical diagnostic tests on a relatively large scale. Cross reactivity with HSV-specific antibodies, and, consequent, false-positive results, thus are frequently observed in glycoprotein ELISAs, due to pronounced homology that among glycoproteins of these á-herpesviruses.

SUMMARY OF THE INVENTION

In one embodiment of the invention, an immunoreactive peptide is provided which is homologous with the AA 12 to 235 region of VZV VP26. In another embodiment, a nucleic acid is provided which hybridizes under stringent conditions with a nucleic acid that encodes an immunoreactive peptide that is homologous with the AA 12 to 235 region of VZV VP26 wherein the peptide is recognized by antibodies directed against VZV but not recognized by antibodies which are directed against other herpes-viruses. In yet another embodiment, an immunochemical method is provided for detecting antibodies against VZV in a sample, comprising the step (a) contacting an immunoreactive peptide as described in claim 1 with the sample and (b) determining binding between antibody in the sample and the peptide. Another embodiment of the invention is a method for detecting VZV from a sample comprising the steps of contacting a nucleic acid as described above with the sample to allow hybridiztion of the nucleic acid, and determining the presence of nucleic acid hybrid formed. Yet another embodiment is a test kit for detecting antibodies against VZV, which comprises an immunoreactive peptide as described above or a nucleic acid which codes for such an immunoreactive peptide.

BRIEF DESCRIPTION OF THE FIGURES

FIGS. 1(a), 1(b) and 1(c) depict a nucleotide sequence (SEQ ID NOS 1 and 2) that corresponds with amino acid residues 1–235 of VP26 (ORF23) (Ellen strain). This contains a total of 235 AA and has a theoretical molecular weight of 24.4 kDa. The region in bold corresponds to an AA 12–235 VP26* immunoreactive fragment having a total of 224 amino acids and a theoretical molecular weight of 23 kDa. The rhombus (#) symbolizes a stop codon. The numbering of the amino acids begins with a methionine start codon of the published ORF23 sequence (A. J. Davison & J. E. Scott. (1986), J. Gen. Virol. 67, 1759–1816).

FIG. 2 shows data obtained from an ELISA test in accordance with an embodiment of the invention.

FIG. 3 shows data obtained from another ELISA test in accordance with an embodiment of the invention.

DETAILED DESCRIPTION OF THE INVENTION

A possible solution to the above-cited problems lies in the use of recombinant proteins, which can be prepared in large quantity in a heterologous system, e.g. in *Escherichia coli* (*E. coli*). There is no possibility of infecting personnel with VZV in this system. The use of recombinant protein also allows differential diagnosis directed towards specific viral protein. In particular, the reactive region of an VZV protein can be delimited to such an extent that cross reactivities with antibodies that are specific for other herpesviruses can be virtually or completely ruled out. A protein which meets these requirements can be expressed as a hybrid protein, with either a host-specific protein, for example the *E. coli* maltose-binding protein (MBP) or an N-terminally located sequence of 6 histidine residues (His tag), contributing, as the fusion partner, stability of the expression product. These hybrid proteins can, by way of single-step affinity purification, be used directly, in almost pure, and consequently contamination-free form, for coating diagnostically utilizable surfaces, for example ELISA microtitration plates.

Unfortunately, proteins which meet the above-mentioned criteria have not been described for the VZV system. The possible solution thus poses additional problems to be overcome in order to make and use a suitable *varicella zoster* diagnostic test.

Surprisingly, stable expression of a part of VZV ORF23, as VP26*, was found in *E. coli*. It was furthermore found, surprisingly, that VP26* is immunoreactive and can be employed advantageously in diagnosis.

The present invention consequently relates to an immunoreactive peptide (a peptide that cross-reacts with antibody specific to VP26) that is homologous with the AA 12 to 235 region of VZV VP26 or which essentially comprises the amino acids 12 to 235 region of VP26. By "essentially comprises the amino acids 12 to 235 region of VP26" is meant a homologous portion of this region that maintains an epitope of the the VP26, as easily determined by cross-reactivity with antibody against VP26. The term "essentially" refers to the fact that the entire region is not required for an epitopic structure and in fact, the skilled artisan readily appreciates that peptides as short as 10 amino acids long can be selected, based on the information provided by the specification, that can work according to the invention. In one embodiment according to this definition, a homologous portion is less than the total region but greater than 10 amino acids long, which is sufficient to form an epitope characteristic of this region. In another embodiment, the homologous portion is between 10 and 26 amino acids long. In yet another embodiment, the homologous portion is between 26 and 50 amino acids long. In yet another embodiment the homologous portion is between 50 and 223 amino acids long.

Immunoreactive peptides that display naturally varying amino acid sequences due to VZV strain variations are expressly included in this context. The term "homologous" as used here, has the customary meaning known to the skilled artisan. The term means, according to one embodiment of the invention, in reference to a comparison of two peptides or proteins, that when the sequences of the two molecules are aligned side by side, the degree of correspondence (% identical amino acids at the positions) is equal to or less than the variation that is possible within naturally occurring sequences. In one embodiment of the invention this variation is equal or less than 5%. In another embodiment this variation is equal to or less than 7%. In yet another embodiment, this variation is equal to or less than 10%. In such embodiments, the sequence can be modified easily and still remain immunoreactive, and thus useful for the invention. Still further, conservative amino acid changes can be made (as known to the skilled artisan) which maintain immunoreactivity.

The invention furthermore relates to nucleic acids, i.e. DNA or RNA, which encode the above-mentioned immunoreactive peptides according to the invention. More specifically nucleic acid having a sequence depicted in FIG. 1 is contemplated. However, in addition to this, nucleic acids are contemplated which hybridize with the above-mentioned nucleic acids under stringent conditions as used herein and also as described in references cited herein. These nucleic acids encode peptides that are recognized by antibodies which are directed against VZV but which are not recognized by antibodies that are directed specifically against other herpesviruses.

The stringency of hybridization used in the invention is determined by a number of factors during hybridization and during the washing procedure including temperature, ionic strength, length of time and concentration of formamide. These factors are outlined in, for example, Sambrook et al. (Sambrook et al., *Molecular Cloning A Laboratory Manual* $2^{nd}Ed.$, 1989 Cold Spring Harbor Laboratory Press, Cold Spring Harbor, N.Y. which is incorporated by reference).

The invention also relates to immunoreactive peptides that can be prepared by expressing nucleic acid having the sequence depicted in FIG. 1 or one of the above-mentioned nucleic acids which hybridizes under stringent conditions, wherein all of the expressed peptides are recognized by antibodies which are directed against VZV but not by antibodies which are directed against other herpesviruses. In particular, the invention particularly relates to peptides that comprise the AA 12 to 235 region of VZV VP26. Moreover, peptides which "essentially comprise" this region are included, as this term, as used herein, means peptides that include antigenically similar sequences to the AA12 to 235 region described herein. Of course, peptides that comprise this region, with only conservative amino acid changes, (basic for basic, neutral hydrophilic for neutral hydrophilic etc. as is known to the skilled artisan) also are useful and are contemplated for the invention.

The invention furthermore relates to an immunochemical method which makes it possible to detect antibodies against VZV. In this method, one or more of the immunoreactive peptides is/are brought into contact with a sample, for example a blood, plasma or serum sample from a patient, which is to be investigated for the presence of VZV-specific antibodies. Methods with which the skilled person is familiar are then used to establish whether antibodies from the sample bind to the immunoreactive peptides employed or enter into another immunological interrelationship, for example a competition, with these peptides.

The present invention also relates to the use of the above-mentioned nucleic acid according to the invention for detecting VZV by means of nucleic acid hybridization.

The present invention furthermore relates to a test kit for detecting antibodies against VZV, which kit comprises an immunoreactive peptide according to the invention, and to a test kit for detecting VZV, which kit comprises a nucleic acid according to the invention.

In order to locate diagnostically utilizable immunoreactive regions, immunoreactive proteins of VZV were identified by immunoscreening a VZV genomic library. For this, a VZV genomic library was constructed as a phage library in the Zap Express System (Stratagene). This library was then used to carry out an immunoscreening employing a serum pool composed of 25 VZV-reactive human serum. The DNA of clones which were assessed as positive were converted into circular forms, sequenced and assigned to corresponding regions of the VZV sequence. Via this method, it was possible to isolate an immunoreactive clone which expressed AA12–235 of ORF23. No expression product for this reading frame had previously been reported in the VZV system. However, it is known from studies of homology between VZV and HSV that ORF23 corresponds to HSV1 UL36 (A. J. Davison & J. E. Scott. (1986), J. Gen. Virol. 67, 1759–1816). However, at 116 AA, the corresponding herpes simplex virus gene product is substantially shorter and also does not exhibit any marked homology. It had not previously been possible to demonstrate any immunoreactivity (of human sera) to either the gene product of VZV ORF23 or the gene product of HSV UL36. On the basis of the above results, the ORF23 gene product (VP26) constitutes a possible candidate for a diagnostic test method. As a consequence, both the entire ORF23 and the N-terminal truncated region were subcloned into vector pMAL-c2. This resulted in the constructs pMAL-VP26 and pMAL-VP26*. These constructs were sequenced in an overlapping, bidirectional manner. The sequence obtained does not display any differences as compared with the published sequence (A. J. Davison & J. E. Scott. (1986), J. Gen. Virol. 67, 1759–1816). Expression of these constructs showed that while it was possible to express the truncated protein stably this was not the case with the whole protein. The pMAL-VP26* product gave a positive immunoreaction with the serum pool (see above). The immunoreactivity also was confirmed after the VZV-specific DNA fragment had been subcloned from vector pMAL-VP26* into vector pQE30 and expressed in the pQE system. It was therefore possible to rule out any possible false-positive assessment arising from the MBP fusion moiety.

In an ELISA assessment, pMAL-VP26* was found, with a calculated cut off=187 (average value of the negative sera+3 times the standard deviation) to give a sensitivity of 69% (n=13) and a specificity of 98% (n=41) or, with a freely selected cut off of 120, a sensitivity of 85% and a specificity of 95%, for IgM diagnosis. When pQE-VP26* was used, the sensitivity with the calculated cut off=173 (average value of the negative sera+3 times the standard deviation) was 62% (n=13) with the specificity being 100% (n=41) or, with a freely selected cut off of 150, the sensitivity was 77% and the specificity was 95%.

In an IgG ELISA assessment, pMAL-VP26* was found, with a calculated cut off at 210 (average value of the negative sera+3 times the standard deviation), to give a sensitivity of 35% (n=49) and a specificity of 100% (n=5) or, with a freely selected cut off at 100, a sensitivity of 59% and a specificity of 80%, for IgG diagnosis. When pQE-VP26* was used, the sensitivity with the calculated cut off of 215 (average value of the negative sera+3 times the standard deviation) was 53% with the specificity being 100%, and, with the freely selected cut off at 130, the sensitivity was 82% and the specificity was 80%.

EXAMPLES

Example 1

Isolation of Viral VZV Virions and DNA extraction

Sonication was used to release virions from VZV-infected fibroblasts. The viruses were purified from cell constituents through a linear sucrose gradient (20–70% (w/v)). Following incubation with DNase I, viral DNA was released from the virions by treating them with proteinase K and sodium dodecyl sulfate (SDS). After having been extracted with phenol/chloroform, the viral DNA was precipitated with ethanol.

Example 2

Construction of a Genomic Expression Library and Immunoscreening:

The VZV genomic DNA (see Example 1) was partially digested by incubating with the restriction enzyme SauIIIA and then cloned into the BamHI cleavage site of lambda DNA of the ZAP Express vector system (Stratagene) and packaged in lambda phages. Following infection of *E. coli* (XL1-Blue MRF), the phage titer was found to be $5\times10^5$/ml. By means of blue/white screening it was established that 25% of these phages did not harbor any inserted DNA fragments. XL1-Blue cells were infected with the phages, transferred to LB top agar and incubated at 42° C. for 3 hours on LB agar plates. After laying isopropyl-â-D-thiogalactopyranoside-soaked nitrocellulose membranes on them, the LB plates were incubated at 37° C. for 6–10 hours. The membranes were then analyzed for immunoreactive clones by means of immunostaining using a serum pool composed of 25 VZV-reactive human sera as the first antibody and a peroxidase-coupled rabbit anti-human IgG as the second antibody. Immunoreactive clones were plaque-purified. The region encoding the phagemid vector pBK/CMV, including the inserted VZV DNA, was excised using the ExAssist helper phage system (Stratagene) and circularized. The VZV DNA moiety was analyzed by sequencing and identified by database searching (GCG Blastn program).

Example 3

Cloning ORF23 (VP26)

The viral DNA (see Example 1) or the phagemid vector, pBK/CMV-23, obtained from the immunoreactive lambda phage served as a template for amplifying the ORF23 (VP26) or, respectively, the ORF23 fragment (VP26*) which was inserted in vector pBK/CMV-23. The following primers were used as amplification oligonucleotides:

VP26:VP26H 5' GGAATTCCGGATGACACAACCCGCATCGTCTCGTGTA 3' (SEQ ID NO: 3);

VP26R 5' GCTCTAGATTACACCTACGACTTCTTGAAGCGTTTCC 3' (SEQ ID NO: 4).

VP26*:VP26*H 5' GGAATTCCGCGCCTGCAGGTCGACACTAGTGGAT 3' (SEQ ID NO: 5)

VP26*R 5' GCTCTAGATTACACCCTACGACTTCTTGAAGCGTTTCC 3' (SEQ ID NO: 4).

These oligonucleotides are complementary to the corresponding segment of the published VZV sequence (A. J. Davison & J. E. Scott. (1986), J. Gen. Virol. 67, 1759–1816) or the sequence of vector pBK/CMV (Stratagene), but they contain, at their 5' termini, a restriction cleavage site sequence which did not hybridize the template DNA. After amplification had taken place, the amplificate, of 726 bp or 714 bp in size, respectively, was cleaved terminally with the restriction enzymes EcoRI and XbaI and ligated into expression vector pMAL-c2, which had been linearized previously with EcoRI and XbaI. The entire ORF23 was completely sequenced in an overlapping, bidirectional manner. The vectors were designated pMAL-VP26 and pMAL-VP26*, respectively. In addition, the region (VP26*) encoding the immunoreactive protein was cloned into vector pQE30. VZV genomic DNA was used as the template DNA. The following primers were used as amplification oligonucleotides:

VP26*:VP26* 5' CGGATCCGATCCCAGCAACCCCAC-
CAC 3'(SEQ ID NO: 6);
VP26R 5' GCTCTAGATTACACCCTACGACTTCT-
TGAAGCGTTTCC 3'(SEQ ID NO: 4).

These oligonucleotides are complementary to the corresponding segment of the published VZV sequence (A. J. Davison & J. E. Scott. (1986), J. Gen. Virol. 67, 1759–1816), but they contain, at their 5' termini, a restriction cleavage site sequence which did not hybridize with the template DNA. After amplification had taken place, the amplificate, which was 690 bp in size, was cleaved terminally with the restriction enzyme EcoRI and ligated into expression vector pQE30, which had been linearized previously with EcoRI and SmaI. The vector was designated pQE-VP26*.

Example 4

Recombinant Proteins pMal-VP26* and pQE-VP26* a) Preparation

Expression and purification of the recombinant protein pMAL-VP26* was carried out by means of affinity chromatography in accordance with the manufacturer's instructions (New England Biolabs, 800–21S). Expression and purification of recombinant protein pQE-VP26* was carried out by means of metal affinity chromatography under native conditions in accordance with the manufacturer's instructions (Clontech, Talon Metal Affinity Resin, PT1320-1).

b) Preparation of solid phase I (novel system)

Type B microtitration plates (from Greiner) were incubated, at 4° C. for 18 hours, with 110 ul per well of coating solution (1 ug of recombinant pMal-VP26*/ml or 1 ug of recombinant pQE-VP26*/ml in 50 mM sodium carbonate buffer, pH 9.5). The wells of the microtitration plates were then washed three times with 300 ul of washing solution on each occasion (50 mM Tris/EDTA, pH 7.0–7.4+ 0.5% BSA).

For testing in an anti-VZV IgG enzyme immunoassay, the recombinant protein pQE-VP26* was coated under the same conditions as described above, but using a concentration of 2 ug/ml.

c) Enzyme immunoassay for detecting anti-VZV IgM antibodies:

The enzyme immunoassay for detecting anti-VZV IgM antibodies was carried out as follows:

Sera were initially diluted 1:84 in POD sample buffer (Behring Diagnostics, OWBE 945) and then preincubated at room temperature for 15 minutes with RF adsorbent (Behring Diagnostics, OUCG 945) in a ratio of 1:2. In each case, 100 ul of the sera which had been prediluted as described above were incubated, at 37° C. for 1 h, in the wells of the microtitration plates which had been prepared as described in Example 4b. After the plates had been washed 3 times with POD wash solution (Behring Diagnostics, OSEW 965), 100 i1 of the anti-human IgM/POD conjugate (Behring Diagnostics, batch 4241313), diluted in Microbiol conjugate buffer (Behring Diagnostics, OUWW 935) in a ratio of 1:25 in the case of pQE-VP26* and 1:50 in the case of pMal-VP26*, were pipetted in. The incubation of 1 hour (at +37° C.) was terminated by 3 further washing steps. The bound peroxidase activity, which correlates directly with the number of bound VZV antibody molecules, was determined by adding $H_2O_2$/tetramethylbenzidine (Behring Diagnostics, OUVG 945). After 30 minutes at room temperature, substrate conversion was stopped by adding 0.5 M sulfuric acid (Behring Diagnostics, OSFA 965) and the extinction was measured at 450 nm. Anti-VZV-positive and anti-VZV-negative sera were investigated both in the Enzygnost anti-VZV/IgM reference system (Behring Diagnostics, OWLW 155) and in the novel enzyme immunoassay. The results (in extinction units) of the investigation are given in FIG. 4. In an ELISA assessment, pMAL-VP26* was found, with a calculated cut off=187 (average value of the negative sera+3 times the standard deviation) to give a sensitivity of 69% (n=13) and a specificity of 98% (n=41) or, with a freely selected cut off of 120, a sensitivity of 85% and a specificity of 95% for IgM diagnosis. When pQE-VP26* is used, the sensitivity with the calculated cut off=173 (average value of the negative sera+3 times the standard deviation) is 62% (n=13) and the specificity is 100% (n=41) or, with a freely selected cut off of 150, the sensitivity is 77% and the specificity is 95%.

Example 5

Enzyme Immunoassay for Detecting Anti-VZV IgG Antibodies

In order to detect anti-VZV IgG antibodies in the enzyme immunoassay, 100 ul of the sera which had been prediluted 1:100 in POD sample buffer (Behring Diagnostics, OWBE 945) were in each case pipetted into the microtiter plate which had been prepared as described in Example 4b and incubated at 37° C. for 1 h. After the plate had been washed 3 times with POD wash solution (Behring Diagnostics, OSEW 965), 100 ul of anti-human IgG/POD conjugate (Behring Diagnostics batch 243713), diluted 1:50 in Microbiol conjugate buffer (Behring Diagnostics, OUWW 935), were pipetted in. The 1-hour incubation (at +37° C.) was terminated with a further three washing steps. The bound peroxidase activity, which correlates directly with the number of bound VZV antibody molecules, was determined by adding $H_2O_2$/tetramethylbenzidine (Behring Diagnostics, OUVG 945). After 30 minutes at room temperature, substrate conversion was stopped by adding 0.5 M sulfuric acid (Behring Diagnostics, OSFA 965) and the extinction was measured at 450 nm.

Anti-VZV-positive and anti-VZV-negative sera were investigated both in the Enzygnost anti-VZV/IgG reference system (Behring Diagnostics, OWLT 155) and in the novel enzyme immunoassay. The results (extinction units) of the investigation are given in FIG. 5.

In an ELISA assessment, pMAL-VP26* was found, with a calculated cut off of 210 (average value of the negative sera+3 times the standard deviation) to give a sensitivity of 35% (n=49) and a specificity of 100% (n=5) or, with a freely selected cut off of 100, a sensitivity of 59% and a specificity of 80%, for IgG diagnosis. When pQE-VP26* is used, the sensitivity with the calculated cut off of 215 (average value of the negative sera+3 times the standard deviation) is 53% and the specificity is 100%, or, with the freely selected cut off at 130, the sensitivity is 82% and the specificity is 80%.

Each reference cited herein is hereby incorporated in its entirety by reference. The priority application 19757765.2 filed Dec. 23, 1997 is herein incorporated ill its entirety by reference.

We claim:

1. An immunoreactive peptide which is homologous with and has less than 10% variation from the AA 12 to 235 region of SEQ ID No: 1.

2. An immunoreactive peptide consisting of the AA 12 to 235 region of SEQ ID NO: 1 of *varicella zoster* virus VP26.

3. An immunochemical method for detecting antibodies against *varicella zoster* virus in a sample, comprising the step (a) contacting an immunoreactive peptide as described in claim 1 with the sample and (b) detecting binding between antibody in the sample and the peptide.

4. A method as described in claim 3, wherein step b is carried out indirectly by competition of the peptide in a solution.

5. A test kit for detecting antibodies against VZV, which comprises an immunoreactive peptide as claimed in claim 1.

* * * * *

SEQUENCE LISTING

<160> NUMBER OF SEQ ID NOS: 6

<210> SEQ ID NO 1
<211> LENGTH: 705
<212> TYPE: DNA
<213> ORGANISM: Varicella Zoster Virus
<220> FEATURE:
<221> NAME/KEY: CDS
<222> LOCATION: (1)..(705)

<400> SEQUENCE: 1

| | | |
|---|---|---|
| atg aca caa ccc gca tcg tct cgt gta gtc ttt gat ccc agc aac ccc<br>Met Thr Gln Pro Ala Ser Ser Arg Val Val Phe Asp Pro Ser Asn Pro<br>1                   5                     10                    15 | | 48 |
| acc aca ttt tcg gtg gaa gca att gcg gct tac acc ccc gtt gct tta<br>Thr Thr Phe Ser Val Glu Ala Ile Ala Ala Tyr Thr Pro Val Ala Leu<br>                  20                     25                     30 | | 96 |
| ata cga ctt tta aac gcc agt gga cct ttg caa cct ggt cac cgt gtg<br>Ile Arg Leu Leu Asn Ala Ser Gly Pro Leu Gln Pro Gly His Arg Val<br>       35                     40                     45 | | 144 |
| gac atc gct gat gcc aga agc att tac acc gtg gga gcc gcg gcc agt<br>Asp Ile Ala Asp Ala Arg Ser Ile Tyr Thr Val Gly Ala Ala Ala Ser<br>50                     55                     60 | | 192 |
| gcc gcg cgt gca cgc gct aac cat aat gca aat acg ata cgc cga acg<br>Ala Ala Arg Ala Arg Ala Asn His Asn Ala Asn Thr Ile Arg Arg Thr<br>65                     70                     75                     80 | | 240 |
| gcc atg ttt gcc gag act gac cct atg aca tgg tta aga cca acg gtt<br>Ala Met Phe Ala Glu Thr Asp Pro Met Thr Trp Leu Arg Pro Thr Val<br>                  85                     90                     95 | | 288 |
| ggc tta aaa cgt acg ttt aac ccg cgt att ata cga cca caa ccc cca<br>Gly Leu Lys Arg Thr Phe Asn Pro Arg Ile Ile Arg Pro Gln Pro Pro<br>                  100                  105                  110 | | 336 |
| aat cca tcc atg agt ttg gga atc tcg ggg cct act ata ttg ccg caa<br>Asn Pro Ser Met Ser Leu Gly Ile Ser Gly Pro Thr Ile Leu Pro Gln<br>       115                     120                     125 | | 384 |
| aaa aca cag agc gcc gat cag tct gct tta caa cag ccc gcc gcg ttg<br>Lys Thr Gln Ser Ala Asp Gln Ser Ala Leu Gln Gln Pro Ala Ala Leu<br>130                     135                     140 | | 432 |
| gcg ttt tcg gga tca tcc ccg caa cac ccc cca cct caa acg acg tcg<br>Ala Phe Ser Gly Ser Ser Pro Gln His Pro Pro Pro Gln Thr Thr Ser<br>145                     150                     155                  160 | | 480 |
| gca tcc gtt gga caa cag caa cac gtg gtg tcg ggg tct tct gga caa<br>Ala Ser Val Gly Gln Gln Gln His Val Val Ser Gly Ser Ser Gly Gln<br>                  165                  170                  175 | | 528 |
| caa ccg caa cag gga gca cag tca agc act gtc cag cca aca acc gga<br>Gln Pro Gln Gln Gly Ala Gln Ser Ser Thr Val Gln Pro Thr Thr Gly<br>                    180                     185                  190 | | 576 |
| tca ccg ccc gcg gcc caa ggc gtg cca cag tct acc ccg ccc cca acc<br>Ser Pro Pro Ala Ala Gln Gly Val Pro Gln Ser Thr Pro Pro Pro Thr<br>       195                     200                     205 | | 624 |
| caa aat acc ccc cag ggg ggt aag gga cag acc ttg tca cac acg gga<br>Gln Asn Thr Pro Gln Gly Gly Lys Gly Gln Thr Leu Ser His Thr Gly<br>210                     215                     220 | | 672 |
| caa tct gga aac gct tca aga agt cgt agg gtg<br>Gln Ser Gly Asn Ala Ser Arg Ser Arg Arg Val<br>225                     230                     235 | | 705 |

<210> SEQ ID NO 2
<211> LENGTH: 235
<212> TYPE: PRT

```
<213> ORGANISM: Varicella Zoster Virus

<400> SEQUENCE: 2

Met Thr Gln Pro Ala Ser Ser Arg Val Val Phe Asp Pro Ser

-continued

```
<223> OTHER INFORMATION: Description of Artificial Sequence: Primer

<400> SEQUENCE: 5
ggaattccgc gcctgcaggt cgacactagt ggat                    34

<210> SEQ ID NO 6
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 6
cggatccgat cccagcaacc ccaccac                             27
```